United States Patent [19]

Wilson et al.

[11] Patent Number: 5,703,265
[45] Date of Patent: Dec. 30, 1997

[54] MONOFUNCTIONAL N—(2—CYANOETHENYL)SULFONAMIDES

[75] Inventors: John C. Wilson; Peter S. Alexandrovich, both of Rochester, N.Y.

[73] Assignee: Eastman Kodak Company, Rochester, N.Y.

[21] Appl. No.: 644,758

[22] Filed: May 10, 1996

[51] Int. Cl.$^6$ .................................................. C07C 255/00
[52] U.S. Cl. ....................................... 558/390; 558/401
[58] Field of Search ....................................... 558/390, 401

[56] References Cited

U.S. PATENT DOCUMENTS

| | | | |
|---|---|---|---|
| 3,577,354 | 5/1971 | Kehl | 252/468 |
| 3,893,934 | 7/1975 | Braun et al. | 252/62.1 |
| 4,002,776 | 1/1977 | Braun et al. | 427/19 |
| 4,464,452 | 8/1984 | Gruber et al. | 430/110 |
| 4,480,021 | 10/1984 | Lu et al. | 430/106.6 |

OTHER PUBLICATIONS

W. Schulz et al in Chem. Ber. 100, pp. 2640–2648 (1967) (German).

*Primary Examiner*—Johann Richter
*Attorney, Agent, or Firm*—John R. Everett

[57] ABSTRACT

A compound having the structure:

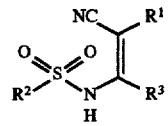

is disclosed. $R^1$ is defined in the specification. The compounds are charged control agents for use in electrostatographic toners and developers.

8 Claims, No Drawings

MONOFUNCTIONAL N—(2-CYANOETHENYL)SULFONAMIDES

FIELD OF THE INVENTION

The present invention relates to charge control agents which are useful in electrostatographic toner compositions. More particularly, the invention relates to N-(2-cyanoethenyl)sulfonamide charge control agents.

CROSS REFERENCE TO RELATED APPLICATIONS

The present application is related to copending, commonly assigned U.S. Ser. No. 08/644,758 entitled: TONER COMPOSITIONS CONTAINING N-(2-CYANOETHENYL)SULFONAMIDES. This related application discloses and claims toner compositions using the compounds of the present application as charge control agents in addition to other N-(2-cyanoethenyl)sulfonamides. Reference is made to this related application for data showing the utility of the compounds of the present invention.

BACKGROUND OF THE INVENTION

In electrography, image charge patterns are formed on a support and are developed by treatment with an electrographic developer containing marking particles which are attracted to the charge patterns. These particles are called toner particles or, collectively, toner. Two major types of developers, dry and liquid, are employed in the development of the charge patterns.

One well-known type of electrostatographic developer comprises a dry mixture of toner particles and carrier particles. Developers of this type are employed in cascade and magnetic brush electro-statographic development processes. The toner particles and carrier paticles differ triboelectrically, such that during mixing to form the developer, the toner particles acquire a charge of one polarity and the carrier particles acquire a charge of the opposite polarity. The opposite charges cause the toner particles to cling to the carrier particles. During development, the electrostatic forces of the latent image, sometimes in combination with an additional applied field, attract the toner particles. The toner particles are pulled away from the carrier particles and become electrostatically attached, in imagewise relation, to the latent image bearing surface. The resultant toner image can then be fixed, by application of heat or other known methods, depending upon the nature of the toner image and the surface, or can be transferred to another surface and then fixed.

Toner particles often include charge control agents, which, desirably, provide high uniform net electrical charge to toner particles without reducing the adhesion of the toner to paper or other medium. Use of charge control agents requires a balancing of shortcomings and desired characteristics to meet a particular situation. Many charge control agents, for example, are colored compounds. Their color makes them less than desirable for use in producing colored images since they interfere with the color rendition of the colorant in the toner composition.

Certain N-(2-cyanoethenyl)sulfonamide compounds are known in the art. The known compounds are all dicyano compounds made by a method that necessarily results in the dicyano compounds. Reference is made to Schulz, et al in *Chem. Ber.*, 100, 2640 (1987). No use is disclosed for the three compounds made in this reference. The compounds have the structures:

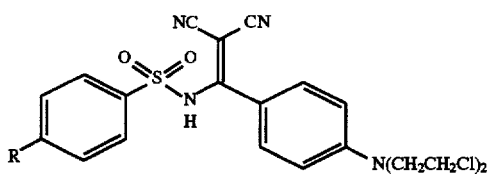

wherein R is hydrogen, $CH_3$ or $NH_2$.

There is a continuing need for negative charge control agents.

SUMMARY OF THE INVENTION

The invention provides a charge control agent having the general structure:

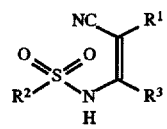

wherein $R^1$ is selected from the group consisting of hydrogen; alkyl containing from 1 to 20 carbons; cycloalkyl containing from 3 to 18 carbons; unsubstituted aromatic ring systems; aromatic ring systems substituted with one or more alkyl, halo, nitro, cyano, hydroxy, alkoxy, carboxy, carboalkoxy, amino, dialkylamino, acyl, trihalomethyl or alkysulfonyl; and heteroaromatic ring systems; said ring systems having a solitary ring or 2 to 3 linked or fused rings, and containing from 3 to 34 carbons; alkanoyl; alkoxycarbonyl; aminocarbonyl; alkylaminocarbonyl; aralkylaminocarbonyl; alkysulfonyl; aroyl; aryloxycarbonyl; arylaminocarbonyl; arylsulfonyl; or aroyl, aryloxycarbonyl, arylaminocarbonyl, aralkylaminocarbonyl or arylsulfonyl substituted with one or more alkyl, hydroxy, alkoxy, carboxy, carboalkoxy, nitro, halo, cyano, amino, dialkylamino, acyl, trihalomethyl or alkysulfonyl; and $R^2$ and $R^3$, which can be the same or different, are independently selected from the group consisting of alkyl containing from 1 to 20 carbons; cycloalkyl containing from 3 to 18 carbons; unsubstituted aromatic ring systems; or aromatic ring systems substituted with one or more alkyl, hydroxy, alkoxy, carboxy, carboalkoxy, nitro, halo, cyano, amino, dialkylamino, acyl, trihalomethyl or alkysulfonyl; heteroaromatic ring systems; said ring systems having a solitary ring or 2 to 3 linked or fused rings, and containing from 3 to 34 carbons; and $R^3$ may also be ethenyl, unsubstituted or substituted with alkyl containing from 1 to 20 carbons or aryl containing from 5 to 10 carbons or aryl substituted with alkyl, hydroxy, carboxy, carboalkoxy, nitro, halo, cyano, amino, dialkylamino, acyl, trihalomethyl, or alkysulfonyl.

DESCRIPTION OF PREFERRED EMBODIMENTS

The term "charge control," as used herein, refers to a propensity of a toner addendum to modify the triboelectric charging properties of the resulting toner.

The compounds of the present invention, are sulfonamides and have the general structure:

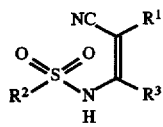 (1)

wherein the various substituents are as described above. It is noted that in comparison to the definition in the above identified related application, $R^1$ here can not be cyano. Thus, the compounds of the Schulz, et al cited above are excluded from the compounds of the present invention. In addition, the compounds of the present invention, not being dicyano compounds, can not be made using the method of Schulz, et al.

It is to be understood that the general structure (1) set forth above includes both geometrical isomers:

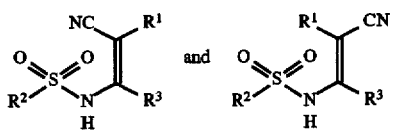

where $R^1$, $R^2$ and $R^3$ are as defined above.

It is also to be understood that the sulfonamides of the invention can tautomerize. Thus, structure (1) could, in many cases, also be represented:

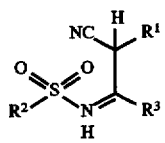

For the sake of brevity, alternate geometric isomeric and tautomeric forms will not be illustrated herein. However, structural formulas should be understood to be inclusive of these alternate forms.

The charge control agents of the invention also are essentially colorless and exhibit excellent thermal stability in air.

It is preferred that one and preferrably both of $R^2$ and $R^3$ be aromatic. Where $R^2$ and $R^3$ are alkyl, the charging rate is less than desired. Thus, embodiments of the sulfonamides of the invention which are currently preferred, can be represented by the general structure:

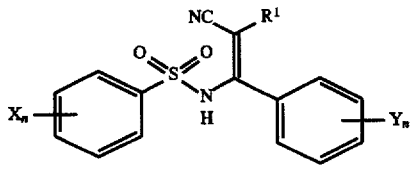

wherein X and Y, each of which can be the same or different, are hydrogen, alkyl, hydroxy, alkoxy, carboxy, carboalkoxy, halo, nitro, cyano, amino, dialkylamino, acyl, trihalomethyl or alkylsulfonyl and $R^1$ is as defined above; and each n is independently an integer of from 0 to 5.

The currently most preferred embodiments of the sulfonamides of the invention can be represented by the general structure:

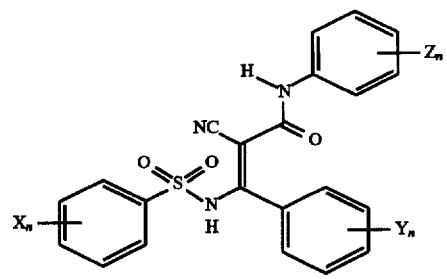

wherein X and Y are as defined above and Z, each of which can be the same or different, is hydrogen, alkyl, hydroxy, alkoxy, carboxy, carboalkoxy, halo, nitro, cyano, amino, dialkylamino, acyl, trihalomethyl or alkylsulfonyl; and each n is independently an integer of from 0 to 5.

Specific examples of sulfonamide charge control agents of the invention are:

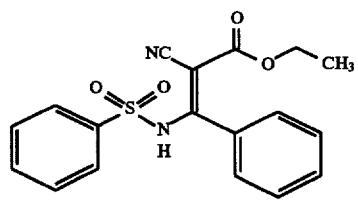

Z-11 melting point of 101–105° C.

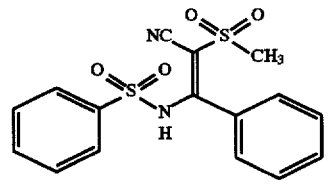

Z-12 melting point of 143–151° C.

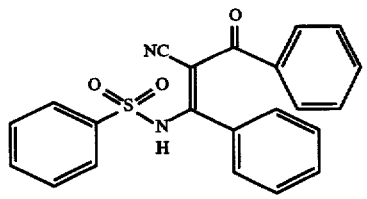

Z-13 melting point of 141–142.5° C.

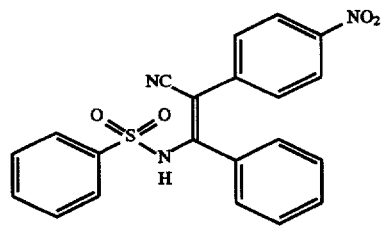

Z-14 melting point of 149.5–151.5° C.

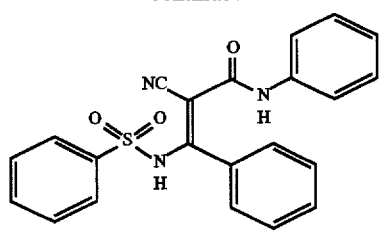

Z-15 melting point of 224.5–226° C.

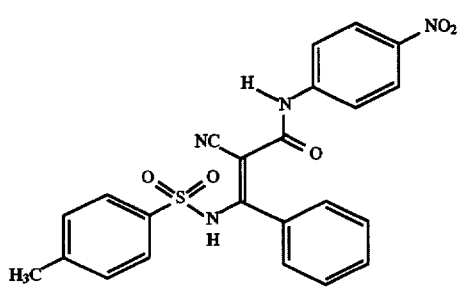

Z-16 decomposes at 291° C.

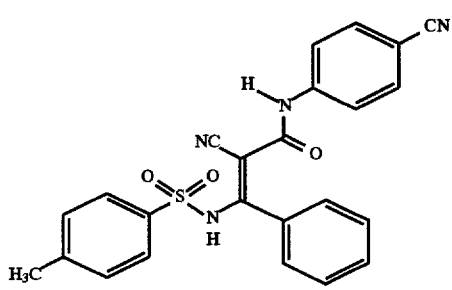

Z-17 decomposes at 280° C.

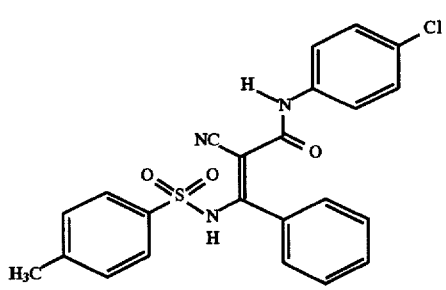

Z-18 melting point 226.5–228.5

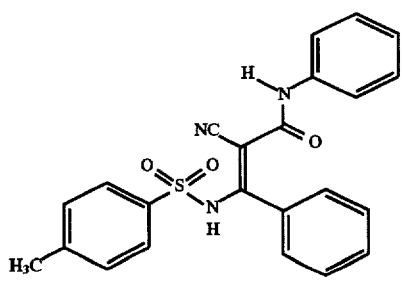

Z-19 melting point 195–198° C.

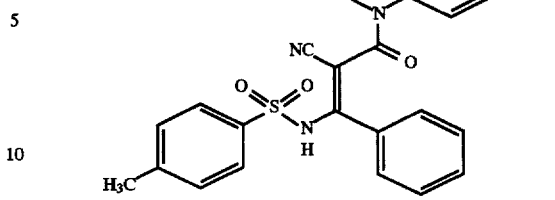

Z-20 melting point 182–185° C.

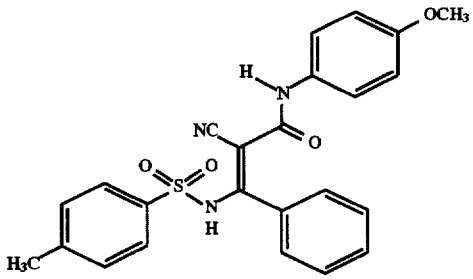

Z-21 melting point 219–221° C.

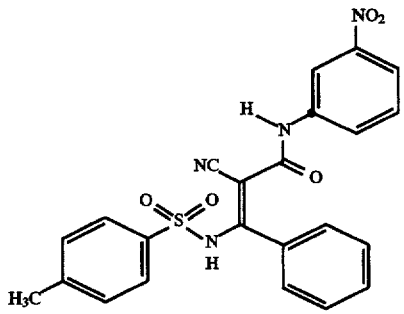

Z-22 melting point 202–204° C.

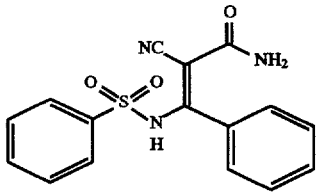

Z-23 melting point 187–189° C.

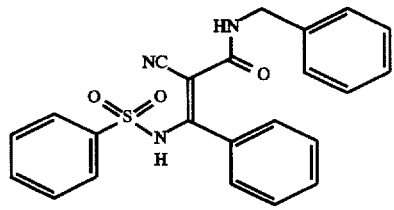

Z-26 melting point 197–199.5° C.

The currently preferred compounds are Z-16, Z-17, Z-18, Z-21 and X-22. These compounds, within the preferred structure, have excellent combinations of properties.

The sulfonamides useful in the invention can be prepared in accordance with the following reaction scheme:

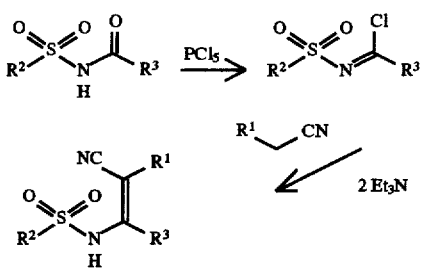

The first reaction is generally known in the art and is described for example in Barnikow and Richter, Z, Chem., 20(3), 97(1980) the second reaction is known in the context of saccharin chemistry but has not been applied to compounds similar to the present invention. Reference is made to Melchiorre, et al; Ann. Chim. (Rome) 1971, 61(6), 399.

The invention is further illustrated by the following Examples. N-acylsulfonamides were prepared by the method disclosed by Kemp and Stephen, J. Chem. Soc., 1948, 11. N-sulfonylcarboximidoyl chlorides were prepared by the method disclosed by Barnikow and Richter, Z. Chem., 20(3), 97 (1980). 2-Cyanoacetamides were prepared by the method disclosed in Ried and Schleimer, Ann., 626, 98 (1959). All other chemicals were commercially available. All melting points for the compounds described above are uncorrected. Thermal stabilities (TGA) in air were determined with a Perkin-Elmer Series 7 Thermal Analysis System at a heating rate of 10° C./min from 25°–500° C. Elemental analyses were performed by combustion techniques. NMR, IR and elemental analysis confirmed the proposed structure in each case.

EXAMPLE

Preparation of Charge Control Agent

A representative synthesis for charge control agent Z-19 is given below. All of the other charge control agent examples given above were prepared in an analogous manner using the appropriate starting materials.

A sulfonamide charge control agent having the structural formula:

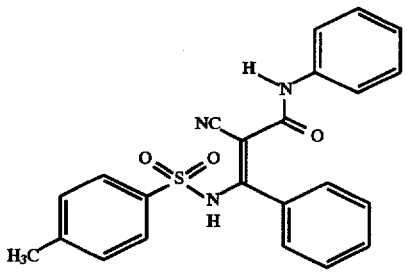

was prepared as follows:

To a mixture of 8.01 g (50 mmol) of 2-cyanoacetanilide, 14.69 g (50 mmol) of N-(4-methylphenylsulfonyl) benzenecarboximidoyl chloride and 200 mL of methylene chloride was added 10.12 g (100 mmol) of triethylamine over 10 minutes followed by 25 mL of methylene chloride rinse. The reaction mixture was stirred for another 1 hr; washed three times with 10% HCl and once with water, dried over magnesium sulfate and concentrated. The solid residue was recrystallized from acetonitrile, collected and dried. The yield of product was 14.64 g (70.1% of theory); mp=195°–198° C.

Elem. analysis for $C_{23}H_{19}N_3 O_3S$: C, 66.17; H, 4.59; N, 10.06; S, 7.68 Found: C, 66.16; H, 4.75; N, 10.03, S, 7.33

The compound was stable in air to 268° C.

While specific embodiments of the invention have been shown and described herein for purposes of illustration, the protection afforded by any patent which may issue upon this application is not strictly limited to a disclosed embodiment; but rather extends to modifications and arrangements which fall fairly within the scope of the claims which are appended hereto.

We claim:

1. A compound having the structure:

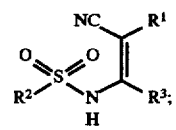

wherein $R^1$ represents hydrogen; alkyl containing from 1 to 20 carbons; cyano, cycloalkyl containing from 3 to 18 carbons, unsubstituted aromatic ring systems, aromatic ring systems substituted with alkyl, halo, nitro, cyano, hydroxy, alkoxy, carboxy, carboalkoxy, amino, dialkylamino, acyl, trihalomethyl or alkysulfonyl; heteroaromatic ring systems (a) having a solitary ring or 2 to 3 linked or fused rings, and (b) containing from 3 to 34 carbons; alkanoyl; alkoxycarbonyl; aminocarbonyl; alkylaminocarbonyl; aralkylaminocarbonyl; alkylsulfonyl; aroyl; aryloxycarbonyl; arylaminocarbonyl; aroyl, aryloxycarbonyl, arylaminocarbonyl, aralkylaminocarbonyl, arylsulfonyl, arylsulfonyl substituted with alkyl, hydroxy, alkoxy, carboxy, carboalkoxy, nitro, halo, cyano, amino, dialkylamino, acyl, trihalomethyl or alkylsulfonyl;

$R^2$ represents alkyl containing from 1 to 20 carbons, cycloalkyl containing from 3 to 18 carbons; unsubstituted aromatic ring systems; aromatic ring systems substituted with alkyl, hydroxy, alkoxy, carboxy, carboalkoxy, nitro, halo, cyano, amino, dialkylamino, acyl, trihalomethyl or alkylsulfonyl; heteroaromatic ring systems (a) having a solitary ring or 2 to 3 linked or fused rings and (b) containing from 3 to 34 carbons; and $R^3$ represents alkyl containing from 1 to 20 carbons, cycloalkyl containing from 3 to 18 carbons; unsubstituted aromatic ring systems; aromatic ring systems substituted with alkyl, hydroxy, alkoxy, carboxy, carboalkoxy, nitro, halo, cyano, amino, dialkylamino, acyl, trihalomethyl or alkylsulfonyl; heteroaromatic ring systems (a) having a solitary ring or 2 to 3 linked or fused rings and (b) containing from 3 to 34 carbons, unsubstituted ethenyl, ethenyl substituted with alkyl containing from 1 to 20 carbons, aryl containing from 5 to 10 carbons or aryl substituted with alkyl, hydroxy, carboxy, carboalkoxy, nitro, halo, cyano, amino, dialkylamino, acyl, trihalomethyl, or alkylsulfonyl.

2. A compound according to claim 1 having the general structure:

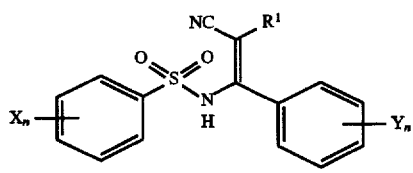

wherein X and Y, each of which can be the same or different, are hydrogen, alkyl, hydroxy, alkoxy, carboxy, carboalkoxy, halo, nitro, cyano, amino, dialkylamino, acyl, trihalomethyl or alkylsulfonyl; and each n is independently an integer of from 0 to 5.

3. A compound according to claim 1 having the general structure:

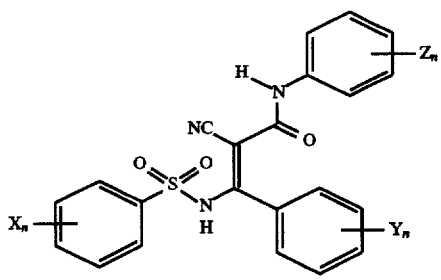

wherein X and Y, each of which can be the same or different, are hydrogen, alkyl, hydroxy, alkoxy, carboxy, carboalkoxy, halo, nitro, cyano, amino, dialkylamino, acyl, trihalomethyl or alkylsulfonyl; Z, each of which can be the same or different, is hydrogen, alkyl, hydroxy, alkoxy, carboxy, carboalkoxy, halo, nitro, cyano, amino, dialkylamino, acyl, trihalomethyl or alkylsulfonyl; and each n is independently an integer of from 0 to 5.

4. A compound according to claim 3 having the formula:

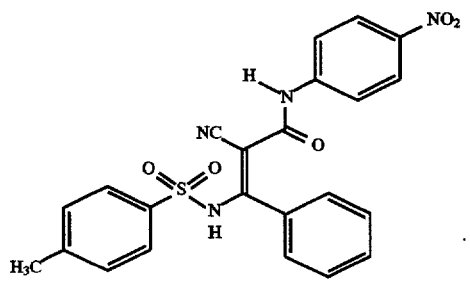

5. A compound according to claim 3 having the formula:

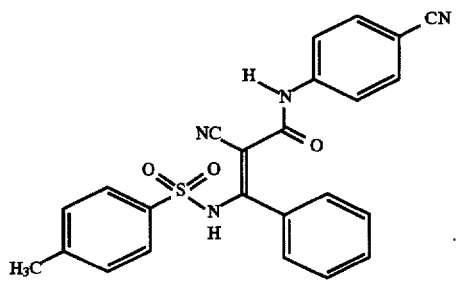

6. A compound according to claim 3 having the formula:

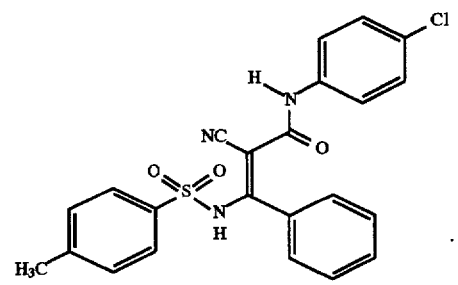

7. A compound according to claim 3 having the formula:

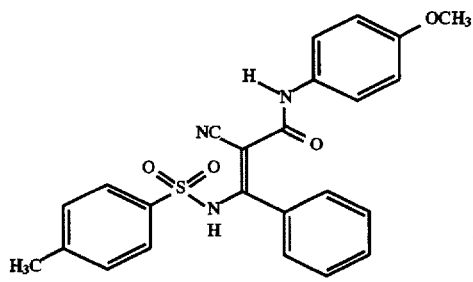

8. A compound according to claim 3 having the formula:

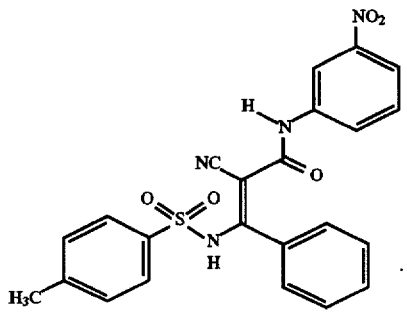

* * * * *